United States Patent
Suruga et al.

(10) Patent No.: US 11,925,107 B2
(45) Date of Patent: Mar. 5, 2024

(54) ORGANIC ELECTROLUMINESCENT DEVICE

(71) Applicant: Hodogaya Chemical Co., Ltd., Tokyo (JP)

(72) Inventors: Kazuyuki Suruga, Tokyo (JP); Shuichi Hayashi, Tokyo (JP); Takeshi Yamamoto, Tokyo (JP); Kouki Kase, Tokyo (JP); Shunji Mochizuki, Tokyo (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 256 days.

(21) Appl. No.: 16/495,523

(22) PCT Filed: Mar. 2, 2018

(86) PCT No.: PCT/JP2018/008131
§ 371 (c)(1),
(2) Date: Sep. 19, 2019

(87) PCT Pub. No.: WO2018/180215
PCT Pub. Date: Oct. 4, 2018

(65) Prior Publication Data
US 2020/0013958 A1 Jan. 9, 2020

(30) Foreign Application Priority Data

Mar. 28, 2017 (JP) .................................. 2017-063510

(51) Int. Cl.
| | | |
|---|---|---|
| *H01L 51/00* | (2006.01) | |
| *C07C 211/54* | (2006.01) | |
| *C07C 211/61* | (2006.01) | |
| *C09K 11/06* | (2006.01) | |
| *H10K 85/60* | (2023.01) | |

(Continued)

(52) U.S. Cl.
CPC .......... *H10K 85/631* (2023.02); *C07C 211/54* (2013.01); *C07C 211/61* (2013.01); *C09K 11/06* (2013.01); *H10K 85/633* (2023.02); *C07C 2603/18* (2017.05); *C09K 2211/1007* (2013.01); *C09K 2211/1011* (2013.01); *C09K 2211/1014* (2013.01); *H10K 50/15* (2023.02); *H10K 50/17* (2023.02); *H10K 85/615* (2023.02); *H10K 85/626* (2023.02)

(58) Field of Classification Search
CPC ................................................ C07C 2603/18
See application file for complete search history.

(56) References Cited

U.S. PATENT DOCUMENTS

| | | | | |
|---|---|---|---|---|
| 10,749,115 B2 * | 8/2020 | Denker | ................. | H01L 51/006 |
| 11,056,653 B2 * | 7/2021 | Yokoyama | ........... | H10K 85/657 |
| 11,158,813 B2 * | 10/2021 | Kabasawa | ............ | H10K 85/626 |

(Continued)

FOREIGN PATENT DOCUMENTS

| | | | | |
|---|---|---|---|---|
| EP | 2684932 A1 * | 1/2014 | ............. | H05B 33/20 |
| JP | 2014-110135 A | 6/2014 | | |

(Continued)

OTHER PUBLICATIONS

International Search Report dated May 22, 2018, issued for PCT/JP2018/008131.

(Continued)

*Primary Examiner* — Alexander R Pagano
(74) *Attorney, Agent, or Firm* — Locke Lord LLP; James E. Armstrong, IV; Nicholas J. DiCeglie, Jr.

(57) ABSTRACT

To provide an organic EL device having low driving voltage, high luminous efficiency, and particularly a long lifetime by combining various materials for an organic EL device having excellent hole and electron injection/transport performances, electron blocking ability, stability in a thin-film state, and durability as materials for an organic EL device having high luminous efficiency and high durability so as to allow the respective materials to effectively reveal their characteristics. In the organic EL device having at least an anode, a hole injection layer, a hole transport layer, a light emitting layer, an electron transport layer, and a cathode, in this order, the hole injection layer includes an arylamine compound of the following general formula (1) and a radialene derivative of the following general formula (2).

[Chemical Formula 1]

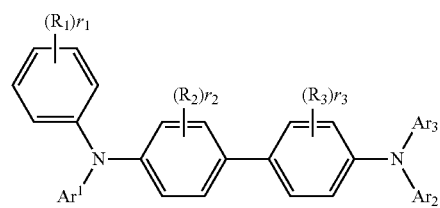

[Chemical Formula 2]

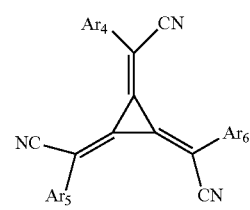

3 Claims, 1 Drawing Sheet

(51) Int. Cl.
  *H10K 50/15* (2023.01)
  *H10K 50/17* (2023.01)

(56) References Cited

U.S. PATENT DOCUMENTS

| | | | | |
|---|---|---|---|---|
| 11,283,026 B2* | 3/2022 | Adachi | | C07D 471/14 |
| 11,437,583 B2* | 9/2022 | Kase | | H10K 85/625 |
| 11,605,785 B2* | 3/2023 | Hirayama | | H10K 85/615 |
| 2008/0265216 A1* | 10/2008 | Hartmann | | C07C 13/04 |
| | | | | 252/500 |
| 2010/0102709 A1* | 4/2010 | Zeika | | C07C 255/51 |
| | | | | 313/504 |
| 2010/0288362 A1* | 11/2010 | Hatwar | | H01L 51/5278 |
| | | | | 136/263 |
| 2013/0105787 A1* | 5/2013 | Tanaka | | H01L 51/0072 |
| | | | | 257/40 |
| 2014/0070204 A1* | 3/2014 | Nagao | | H05B 33/14 |
| | | | | 257/40 |
| 2015/0084020 A1* | 3/2015 | Nagao | | H01L 51/5056 |
| | | | | 257/40 |
| 2015/0115241 A1* | 4/2015 | Zoellner | | H01L 51/0058 |
| | | | | 257/40 |
| 2017/0162800 A1* | 6/2017 | Zoellner | | H10K 50/18 |
| 2017/0200899 A1 | 7/2017 | Kim et al. | | |
| 2017/0346015 A1 | 11/2017 | Hayashi et al. | | |
| 2018/0114916 A1 | 4/2018 | Tayashi et al. | | |
| 2018/0362843 A1* | 12/2018 | Hayashi | | C07D 495/14 |
| 2019/0051838 A1* | 2/2019 | Yokoyama | | H10K 50/15 |
| 2020/0035927 A1* | 1/2020 | Kase | | H10K 85/654 |
| 2020/0335703 A1* | 10/2020 | Mochizuki | | C07D 307/91 |
| 2020/0365809 A1* | 11/2020 | Kase | | C07D 403/04 |
| 2020/0395549 A1* | 12/2020 | Kase | | C09K 11/06 |
| 2021/0143326 A1* | 5/2021 | Kabasawa | | H01L 51/0052 |
| 2021/0210693 A1* | 7/2021 | Uehara | | H10K 85/631 |
| 2021/0395269 A1* | 12/2021 | Kase | | H10K 85/6574 |
| 2021/0399224 A1* | 12/2021 | Suruga | | H10K 85/615 |
| 2022/0052273 A1* | 2/2022 | Kase | | H10K 85/615 |
| 2022/0077403 A1* | 3/2022 | Hirayama | | H10K 85/657 |
| 2022/0102632 A1* | 3/2022 | Suruga | | C07D 307/91 |
| 2022/0119360 A1* | 4/2022 | Mochizuki | | C07D 263/62 |
| 2023/0099897 A1* | 3/2023 | Kase | | C07D 405/04 |
| | | | | 257/40 |
| 2023/0101400 A1* | 3/2023 | Izumida | | H10K 50/11 |
| | | | | 257/40 |
| 2023/0138055 A1* | 5/2023 | Izumida | | C09K 11/06 |
| | | | | 257/40 |

FOREIGN PATENT DOCUMENTS

| | | | | |
|---|---|---|---|---|
| JP | 2014110135 A | * | 6/2014 | |
| JP | 2015-518653 A | | 7/2015 | |
| JP | 2016-02437 | * | 2/2016 | |
| TW | 201626615 A | | 7/2016 | |
| WO | WO-2011131185 A1 | * | 10/2011 | H01L 51/002 |
| WO | 2012/008281 A1 | | 1/2012 | |
| WO | 2014/009310 A1 | | 1/2014 | |
| WO | 16/163276 A1 | | 10/2016 | |
| WO | 2017/138569 A1 | | 8/2017 | |

OTHER PUBLICATIONS

Supplementary European Search Report dated Dec. 9, 2020, issued for the corresponding European Patent Application No. 18776764.5.

\* cited by examiner

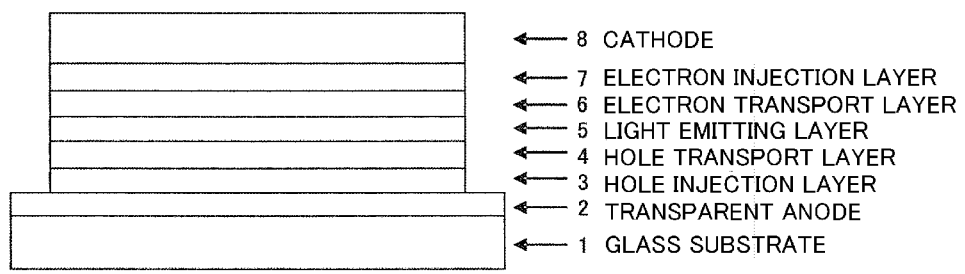

ORGANIC ELECTROLUMINESCENT DEVICE

TECHNICAL FIELD

The present invention relates to an organic electroluminescent device which is a preferred self-luminous device for various display devices. Specifically, this invention relates to organic electroluminescent devices (hereinafter referred to as organic EL devices) using specific arylamine compounds doped an electron acceptor.

BACKGROUND ART

The organic EL device is a self-luminous device and has been actively studied for their brighter, superior visibility and the ability to display clearer images in comparison with liquid crystal devices.

In 1987, C. W. Tang and colleagues at Eastman Kodak developed a laminated structure device using materials assigned with different roles, realizing practical applications of an organic EL device with organic materials. These researchers laminated an electron-transporting phosphor and a hole-transporting organic substance, and injected both charges into a phosphor layer to cause emission in order to obtain a high luminance of 1,000 cd/m$^2$ or more at a voltage of 10 V or less (refer to PTLs 1 and 2, for example).

To date, various improvements have been made for practical applications of the organic EL device. Various roles of the laminated structure are further subdivided to provide an electroluminescence device that includes an anode, a hole injection layer, a hole transport layer, a light emitting layer, an electron transport layer, an electron injection layer, and a cathode successively formed on a substrate, and high efficiency and durability have been achieved by the electroluminescence device (refer to NPL 1, for example).

Further, there have been attempts to use triplet excitons for further improvements of luminous efficiency, and the use of a phosphorescence-emitting compound has been examined (refer to NPL 2, for example).

Devices that use light emission caused by thermally activated delayed fluorescence (TADF) have also been developed. In 2011, Adachi et al. at Kyushu University, National University Corporation realized 5.3% external quantum efficiency with a device using a thermally activated delayed fluorescent material (refer to NPL 3, for example).

The light emitting layer can be also fabricated by doping a charge-transporting compound generally called a host material, with a fluorescent compound, a phosphorescence-emitting compound, or a delayed fluorescent-emitting material. As described in the NPL, the selection of organic materials in an organic EL device greatly influences various device characteristics such as efficiency and durability (refer to NPL 2, for example).

In an organic EL device, charges injected from both electrodes recombine in a light emitting layer to cause emission. What is important here is how efficiently the hole and electron charges are transferred to the light emitting layer in order to form a device having excellent carrier balance. The probability of hole-electron recombination can be improved by improving hole injectability and electron blocking performance of blocking injected electrons from the cathode, and high luminous efficiency can be obtained by confining excitons generated in the light emitting layer. The role of a hole transport material is therefore important, and there is a need for a hole transport material that has high hole injectability, high hole mobility, high electron blocking performance, and high durability to electrons.

Heat resistance and amorphousness of the materials are also important with respect to the lifetime of the device. The materials with low heat resistance cause thermal decomposition even at a low temperature by heat generated during the drive of the device, which leads to the deterioration of the materials. The materials with low amorphousness cause crystallization of a thin film even in a short time and lead to the deterioration of the device. The materials in use are therefore required to have characteristics of high heat resistance and satisfactory amorphousness.

N,N'-diphenyl-N,N'-di(a-naphthyl)benzidine (NPD) and various aromatic amine derivatives are known as the hole transport materials used for the organic EL device (refer to PTLs 1 and 2, for example). Although NPD has desirable hole transportability, its glass transition point (Tg), which is an index of heat resistance, is as low as 96° C., which causes the degradation of device characteristics by crystallization under a high-temperature condition (refer to NPL 4, for example). The aromatic amine derivatives described in the PTL include a compound known to have an excellent hole mobility of 10$^{-3}$ cm$^2$/Vs or higher (refer to PTLs 1 and 2, for example). However, since the compound is insufficient in terms of electron blocking performance, some of the electrons pass through the light emitting layer, and improvements in luminous efficiency cannot be expected. For such a reason, a material with higher electron blocking performance, a more stable thin-film state and higher heat resistance is needed for higher efficiency. Although an aromatic amine derivative having high durability is reported (refer to PTL 3, for example), the derivative is used as a charge transporting material used in an electrophotographic photoconductor, and there is no example of using the derivative in the organic EL device.

Arylamine compounds having a substituted carbazole structure are proposed as compounds improved in the characteristics such as heat resistance and hole injectability (refer to PTLs 4 and 5, for example). Further, it is proposed that hole injectability can be improved by p-doping materials such as trisbromophenylamine hexachloroantimony, radialene derivatives, and F4-TCNQ into a material commonly used for the hole injection layer or the hole transport layer (refer to PTL 6 and NPL 5). However, while the devices using these compounds for the hole injection layer or the hole transport layer have been improved in lower driving voltage, heat resistance, luminous efficiency and the like, the improvements are still insufficient. Further lower driving voltage and higher luminous efficiency are therefore needed.

In order to improve characteristics of the organic EL device and to improve the yield of the device production, it has been desired to develop a device having high luminous efficiency, low driving voltage and a long lifetime by using in combination the materials that excel in hole and electron injection/transport performances, stability as a thin film and durability, permitting holes and electrons to be highly efficiently recombined together.

Further, in order to improve characteristics of the organic EL device, it has been desired to develop a device that maintains carrier balance and has high efficiency, low driving voltage and a long lifetime by using in combination the materials that excel in hole and electron injection/transport performances, stability as a thin film and durability.

CITATION LIST

Patent Literature

PTL 1: P-A-8-048656
PTL 2: Japanese Patent No. 3194657
PTL 3: Japanese Patent No. 4943840
PTL 4: JP-A-2006-151979
PTL 5: WO2008/62636
PTL 6: JP-A-2011-100621

Non Patent Literature

NPL 1: The Japan Society of Applied Physics, 9th Lecture Preprints, pp. 55 to 61 (2001)
NPL 2: The Japan Society of Applied Physics, 9th Lecture Preprints, pp. 23 to 31 (2001)
NPL 3: Appl. Phys. Let., 98, 083302 (2011)
NPL 4: Organic EL Symposium, the 3rd Regular presentation Preprints, pp. 13 to 14 (2006)
NPL 5: Appl. Phys. Let., 89, 253506 (2006)

SUMMARY OF INVENTION

Technical Problem

An object of the present invention is to provide an organic EL device having low driving voltage, high luminous efficiency, and particularly a long lifetime by combining various materials for an organic EL device having excellent hole and electron injection/transport performances, electron blocking ability, stability in a thin-film state, and durability as materials for an organic EL device having high luminous efficiency and high durability so as to allow the respective materials to effectively reveal their characteristics.

Physical properties of the organic EL device to be provided by the present invention include (1) low turn on voltage, (2) low actual driving voltage, (3) high luminous efficiency and high power efficiency, and (4) a long lifetime.

Solution to Problem

For achieving the object, the present inventors, who have focused attention on the fact that an arylamine material doped with a specific electron acceptor is excellent in hole injection and transport performances, stability and durability of a thin film thereof, have produced various organic EL devices in which the material of the hole injection layer is doped with an electron acceptor by selecting a particular arylamine compound (having a particular structure) so as to efficiently perform injection and transport of holes from an anode, and earnestly evaluated the characteristics of the devices. As a result, the present invention has been completed.

Specifically, according to the present invention, the following organic EL devices are provided.

1) An organic EL device comprising at least an anode, a hole injection layer, a hole transport layer, a light emitting layer, an electron transport layer, and a cathode, in this order, wherein the hole injection layer includes an arylamine compound of the following general formula (1) and a radialene derivative of the following general formula (2).

[Chemical Formula 1]

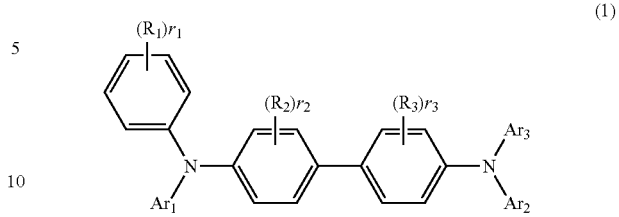

(1)

In the formula, $R_1$ represents a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent. $R_2$ and $R_3$ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy. $r_1$ to $r_3$ may be the same or different, $r_1$ representing 0 to 5, and $r_2$ and $r_3$ representing 0 to 4, where when $r_1$ are 2 to 5, or when $r_2$ and $r_3$ are 2 to 4, $R_1$ to $R_3$, a plurality of which bind to the same benzene ring, may be the same or different and may bind to each other via a single bond, substituted or unsubstituted methylene, an oxygen atom, or a sulfur atom to form a ring. $Ar_1$ to $Ar_3$ may be the same or different, and represent a substituted or unsubstituted aromatic hydrocarbon group, a substituted or unsubstituted aromatic heterocyclic group, or a substituted or unsubstituted condensed polycyclic aromatic group.

[Chemical Formula 2]

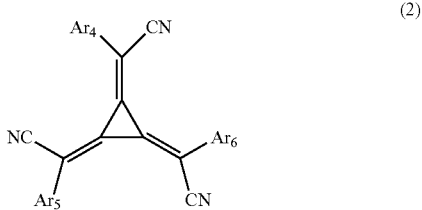

(2)

In the formula, $Ar_4$ to $Ar_6$ may be the same or different, and represent an aromatic hydrocarbon group, an aromatic heterocyclic group, or a condensed polycyclic aromatic group, having an electron acceptor group as a substituent.

2) The organic EL device of 1), wherein the hole transport layer includes a hole transporting arylamine compound.

3) The organic EL device of 1) or 2), wherein the hole transport layer includes an arylamine compound of the general formula (1).

4) The organic EL device of any one of 1) to 3), wherein $Ar_1$ to $Ar_3$ in the general formula (1) represent a substituted or unsubstituted aromatic hydrocarbon group.

5) The organic EL device of any one of 1) to 3), wherein $Ar_1$ to $Ar_3$ in the general formula (1) represent substituted or unsubstituted phenyl, substituted or unsubstituted biphenylyl, substituted or unsubstituted terphenylyl, or substituted or unsubstituted fluorenyl.

Specific examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_1$ to $R_3$ in the general formula (1) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl. When a plurality of these groups bind to the same benzene ring (when $r_1$ is an integer of 2 to 5, or when $r_2$ or $r_3$ is an integer of 2 to 4), these groups may bind to each other via a single bond, substituted or unsubstituted methylene, an oxygen atom, or a sulfur atom to form a ring.

Specific examples of the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R_1$ to $R_3$ in the general formula (1) include a deuterium atom; cyano; nitro; halogen atoms such as a fluorine atom, a chlorine atom, a bromine atom, and an iodine atom; linear or branched alkyloxys of 1 to 6 carbon atoms such as methyloxy, ethyloxy, and propyloxy; alkenyls such as vinyl and allyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, and carbolinyl; disubstituted amino groups substituted by an aromatic hydrocarbon group or a condensed polycyclic aromatic group, such as diphenylamino and dinaphthylamino; disubstituted amino groups substituted by an aromatic heterocyclic group, such as dipyridylamino and dithienylamino; and disubstituted amino groups substituted by substituents selected from aromatic hydrocarbon groups, condensed polycyclic aromatic groups, and aromatic heterocyclic groups. These substituents may be further substituted with the exemplified substituents above. These substituents may bind to each other via a single bond, substituted or unsubstituted methylene, an oxygen atom, or a sulfur atom to form a ring.

Specific examples of the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R_1$ to $R_3$ in the general formula (1) include methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy. When a plurality of these groups bind to the same benzene ring (when $r_1$ is an integer of 2 to 5, or when $r_2$ or $r_3$ is an integer of 2 to 4), these groups may bind to each other via a single bond, substituted or unsubstituted methylene, an oxygen atom, or a sulfur atom to form a ring.

These groups may have a substituent. Examples of the substituent include the same groups exemplified as the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R_1$ to $R_3$ in the general formula (1), and possible embodiments may also be the same embodiments as the exemplified embodiments.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_2$ and $R_3$ in the general formula (1) include phenyl, biphenylyl, terphenylyl, naphthyl, anthracenyl, phenanthrenyl, fluorenyl, indenyl, pyrenyl, perylenyl, fluoranthenyl, triphenylenyl, pyridyl, pyrimidinyl, triazinyl, furyl, pyrrolyl, thienyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, naphthyridinyl, phenanthrolinyl, acridinyl, and carbolinyl.

$R_2$ and $R_3$ may bind to each other via a single bond, substituted or unsubstituted methylene, an oxygen atom, or a sulfur atom to form a ring.

When a plurality of these groups bind to the same benzene ring (when $r_2$ or $r_3$ is an integer of 2 to 4), these groups may bind to each other via a single bond, substituted or unsubstituted methylene, an oxygen atom, or a sulfur atom to form a ring.

These groups may have a substituent. Examples of the substituent include the same groups exemplified as the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R_1$ to $R_3$ in the general formula (1), and possible embodiments may also be the same embodiments as the exemplified embodiments.

Specific examples of the "aryloxy group" in the "substituted or unsubstituted aryloxy group" represented by $R_2$ and $R_3$ in the general formula (1) include phenyloxy, biphenylyloxy, terphenylyloxy, naphthyloxy, anthracenyloxy, phenanthrenyloxy, fluorenyloxy, indenyloxy, pyrenyloxy, and perylenyloxy.

$R_2$ and $R_3$ may bind to each other via a single bond, substituted or unsubstituted methylene, an oxygen atom, or a sulfur atom to form a ring.

When a plurality of these groups bind to the same benzene ring (when $r_2$ or $r_3$ is an integer of 2 to 4), these groups may bind to each other via a single bond, substituted or unsubstituted methylene, an oxygen atom, or a sulfur atom to form a ring.

These groups may have a substituent. Examples of the substituent include the same groups exemplified as the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R_1$ to $R_3$ in the general formula (1), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_3$ in the general formula (1) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_2$ and $R_3$ in the general formula (1).

These groups may have a substituent-, and specific examples of the substituent include a deuterium atom; cyano; nitro; halogen atoms such as a fluorine atom, a chlorine atom, a bromine atom, and an iodine atom; linear or branched alkyls of 1 to 6 carbon atoms such as methyl; linear or branched alkyloxys of 1 to 6 carbon atoms such as methyloxy, ethyloxy, and propyloxy; alkenyls such as vinyl and allyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, and carbolinyl; disubstituted amino groups substituted with an aromatic hydrocarbon group or a condensed polycyclic aromatic group, such as diphenylamino and dinaphthylamino; disubstituted amino groups substituted with an aromatic heterocyclic group, such as dipyridylamino and dithienylamino; and disubstituted amino groups substituted with substituents selected from aromatic hydrocarbon groups, condensed polycyclic aromatic groups, and aromatic heterocyclic groups. These substituents may be further substituted with the exemplified substituents above. These substituents may bind to each other via a single bond, substituted or unsubstituted methylene, an oxygen atom, or a sulfur atom to form a ring.

Specific examples of the "electron acceptor group" in the "aromatic hydrocarbon group, aromatic heterocyclic group, or condensed polycyclic aromatic group having an electron acceptor group as a substituent" represented by $Ar_4$ to $Ar_6$ in the general formula (2) include a fluorine atom, a chlorine atom, a bromine atom, cyano, trifluoromethyl, and nitro.

Examples of the "aromatic hydrocarbon group", the "aromatic heterocyclic group", or the "condensed polycyclic aromatic group" in the "aromatic hydrocarbon group, aromatic heterocyclic group, or condensed polycyclic aromatic group having an electron acceptor group as a substituent" represented by $Ar_4$ to $Ar_6$ in the general formula (2) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_3$ in the general formula (1).

These groups may have a substituent, in addition to the electron acceptor group, and specific examples of the substituent include a deuterium atom; aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; and aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, and carbolinyl. These substituents may be further substituted with the exemplified substituents or electron acceptor groups above. These substituents may bind to each other via a single bond, substituted or unsubstituted methylene, an oxygen atom, or a sulfur atom to form a ring.

$Ar_1$ to $Ar_3$ in the general formula (1) are preferably substituted or unsubstituted fluorenyl, the substituted or unsubstituted aromatic hydrocarbon group, and further preferably, substituted or unsubstituted phenyl, substituted or unsubstituted biphenylyl, substituted or unsubstituted terphenylyl, or substituted fluorenyl. $r_1$ to $r_3$ are preferably 0 to 2, and further preferably 0 or 1.

In the hole injection layer of the organic EL device of the present invention, examples of the electron acceptor doped in the arylamine compound represented by the general formula (1) include a radialene derivative (refers to PTL 6) represented by the general formula (2).

$Ar_4$ to $Ar_6$ in the general formula (2) are preferably an "aromatic hydrocarbon group", a "condensed polycyclic aromatic group", or pyridyl, more preferably phenyl, biphenylyl, terphenylyl, naphthyl, phenanthrenyl, fluorenyl, or pyridyl.

An embodiment in which $Ar_4$ to $Ar_6$ in the general formula (2) are at least partially, preferably completely substituted with an "electron acceptor group" such as a fluorine atom, a chlorine atom, cyano or trifluoromethyl, is preferable.

$Ar_4$ to $Ar_6$ in the general formula (2) are preferably phenyl or pyridyl completely substituted with a fluorine atom, a chlorine atom, cyano, or trifluoromethyl such as tetrafluoropyridyl, a tetrafluoro-(trifluoromethyl)phenyl, cyano-tetrafluorophenyl, dichloro-difluoro-(trifluoromethyl)phenyl, or pentafluorophenyl.

The arylamine compounds of the general formula (1) for preferred use in the organic EL device of the present invention, can be used as a constitutive material of a hole injection layer, an electron blocking layer, or a hole transport layer of an organic EL device. The arylamine compounds of the general formula (1) have high hole mobility and are therefore preferred compounds as material of a hole injection layer or a hole transport layer. Further, the arylamine compounds of the general formula (1) have high electron blocking performance, and are therefore preferred compounds as a material of an electron blocking layer.

The radialene derivatives of the general formula (2) for preferred use in the organic EL device of the present invention are preferred compounds as a p-doping material into a material commonly used for a hole injection layer or a hole transport layer of an organic EL device.

The organic EL device of the present invention combines the materials for an organic EL device excellent in hole injection/transport performances, and stability and durability as a thin film, taking the carrier balance into consideration. Therefore, as compared to conventional organic EL devices, the hole transport efficiency from the anode to the hole transport layer is improved, and thereby the luminous efficiency is improved, and the durability of the organic EL device is improved, while retaining lower driving voltage.

Thus, an organic EL device having low driving voltage, high luminous efficiency, and a long lifetime can be attained.

Advantageous Effects of Invention

The organic EL device of the present invention can efficiently inject and transport a hole into a hole transport layer from an anode, and thus, can improve hole injection and transport efficiency into a light emitting layer by selecting a specific arylamine compound (having a specific structure) capable of effectively exhibiting hole injection and transport roles as a material of a hole injection layer and by p-doping the compound with a specific electron acceptor. The organic EL device of the present invention can achieve an organic EL device having excellent hole injection and transport performances, low driving voltage, and high luminous efficiency An organic EL device having low driving voltage, high luminous efficiency, and a long lifetime can be achieved by selecting the specific arylamine compounds (having the specific structures) as the materials of the hole transport layer without p-doping, and combining the compounds for achieving elaborate carrier balance.

According to the present invention, luminous efficiency, particularly durability can be improved while maintaining low driving voltage of conventional organic EL devices.

BRIEF DESCRIPTION OF DRAWINGS

FIG. 1 is a diagram illustrating the configuration of the organic EL devices of Examples 4 to 6 and Comparative Examples 1 to 2.

DESCRIPTION OF EMBODIMENTS

The following presents specific examples of preferred compounds among the arylamine compounds of the general formula (1) preferably used in the organic EL device of the present invention. The present invention, however, is not restricted to these compounds.

[Chemical Formula 3]

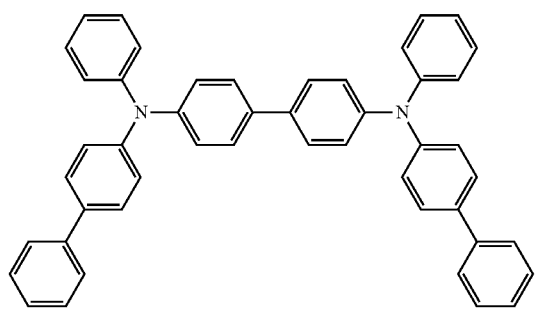

(1-1)

[Chemical Formula 4]

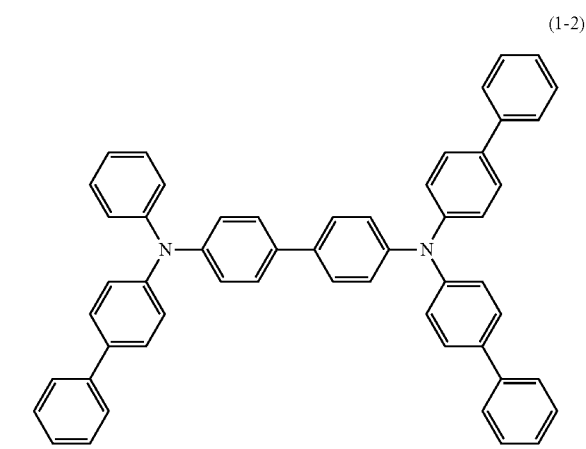

(1-2)

[Chemical Formula 5]

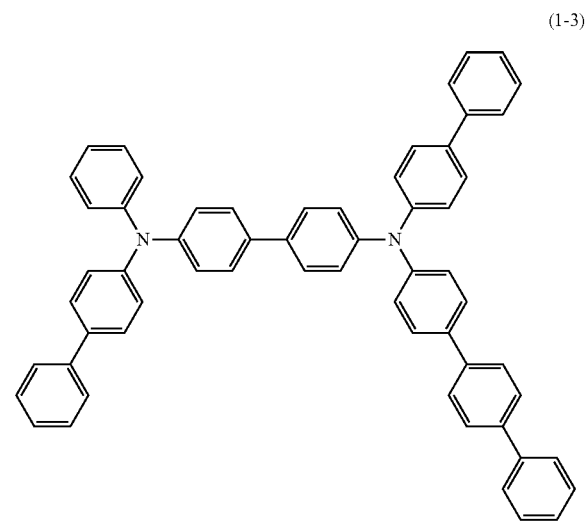

(1-3)

[Chemical Formula 6]

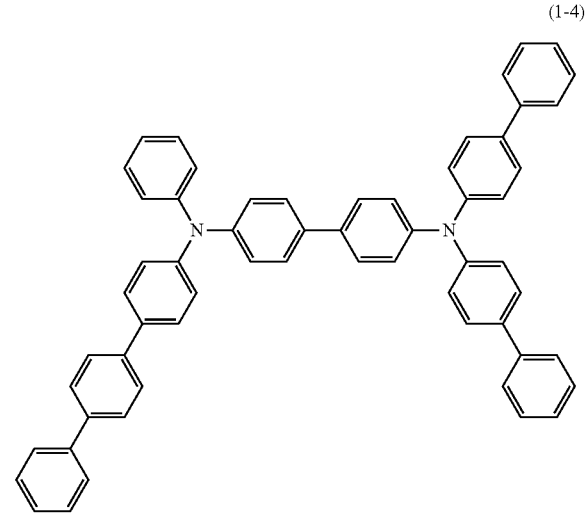

(1-4)

[Chemical Formula 7]
(1-5)
[Chemical Formula 8]
(1-6)
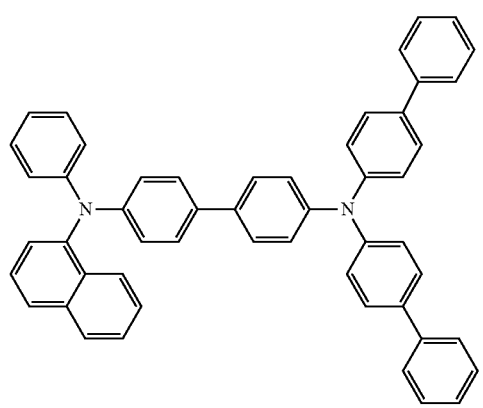
[Chemical Formula 10]
(1-8)
[Chemical Formula 11]
(1-9)
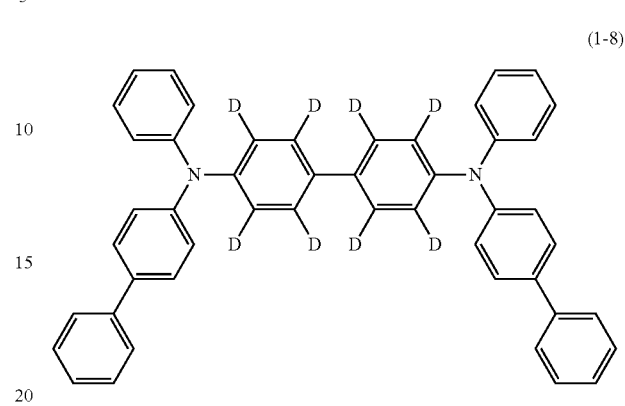
[Chemical Formula 9]
(1-7)
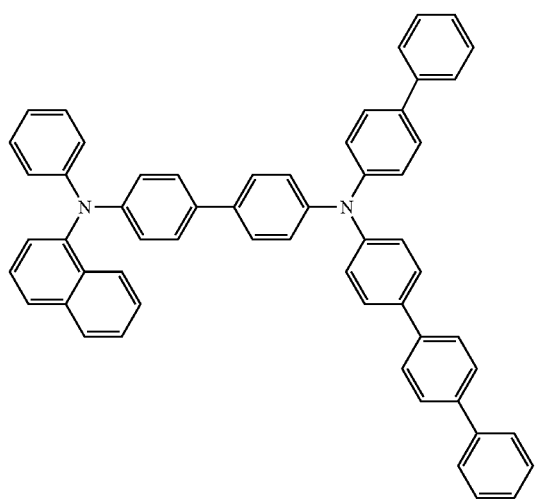
[Chemical Formula 12]
(1-10)
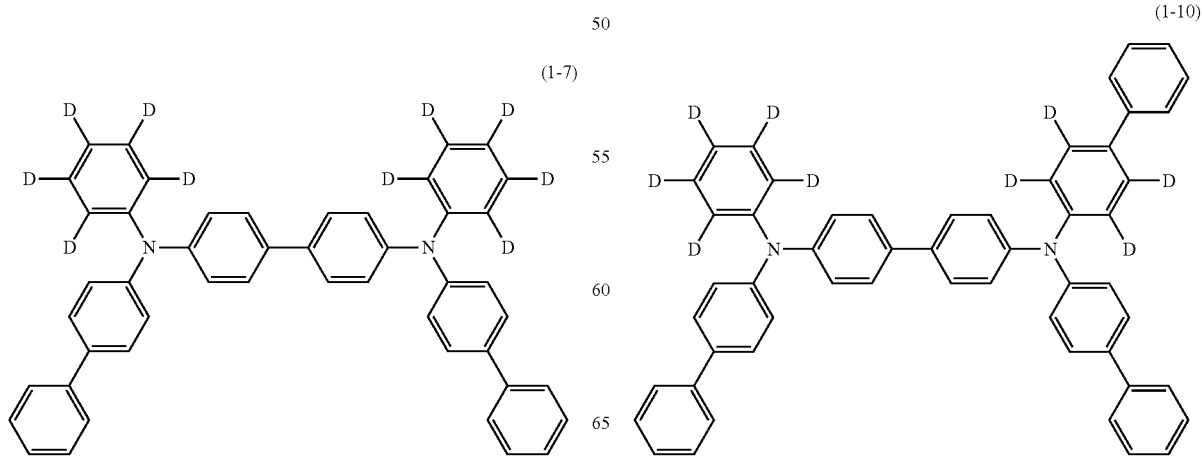

13
-continued
[Chemical Formula 13]
(1-11)
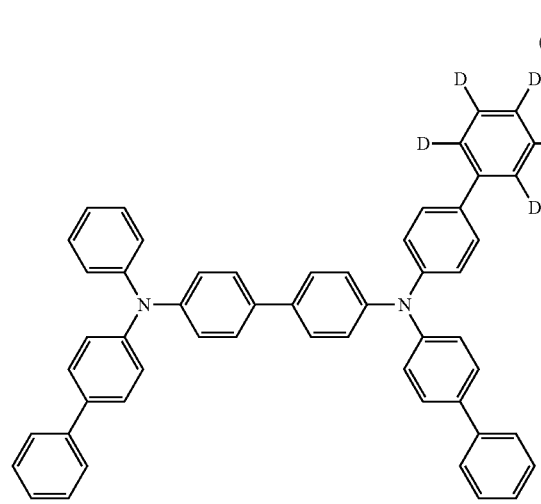
[Chemical Formula 14]
(1-12)
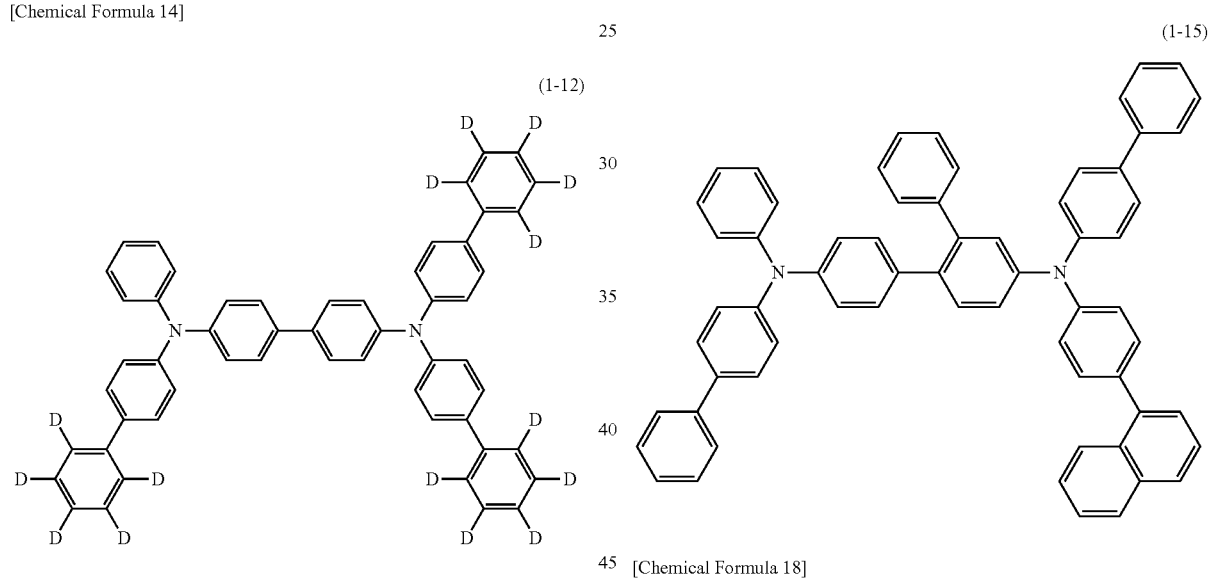
[Chemical Formula 15]
(1-13)
14
-continued
[Chemical Formula 16]
(1-14)
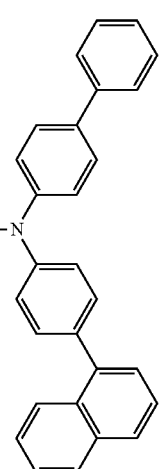
[Chemical Formula 17]
(1-15)
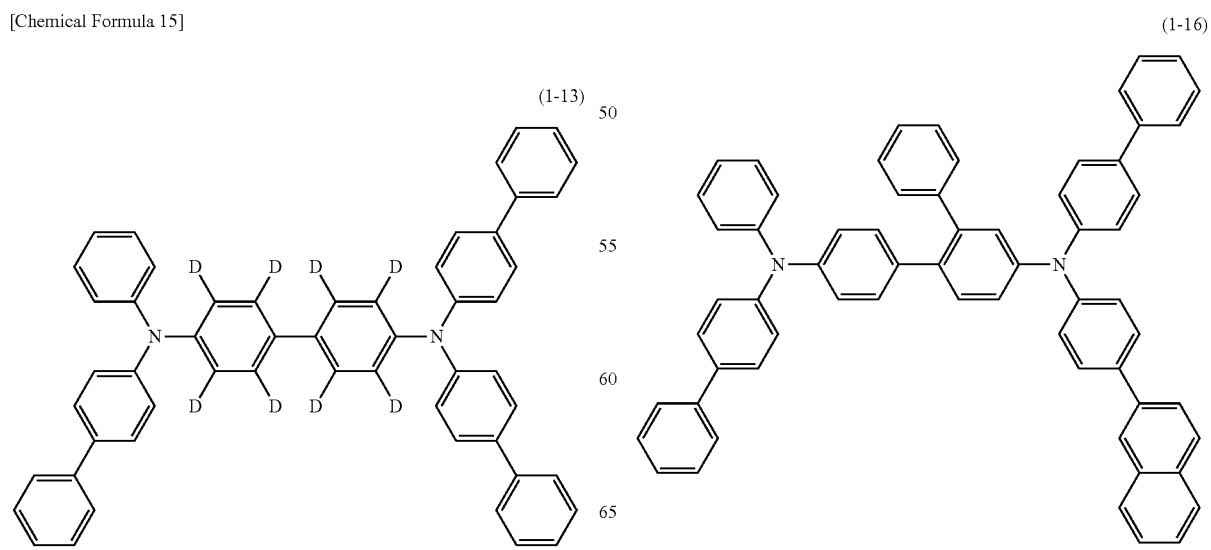
[Chemical Formula 18]
(1-16)
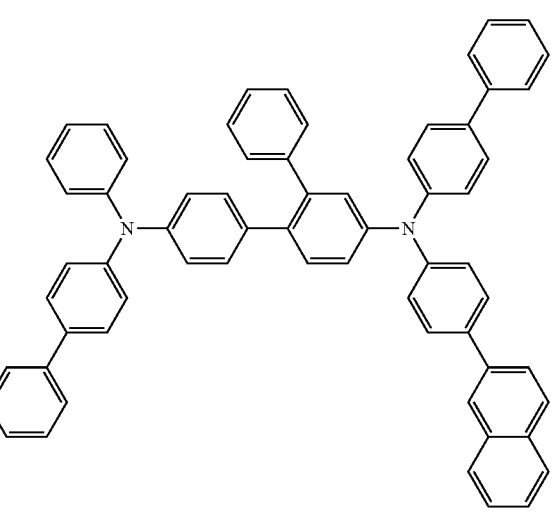

[Chemical Formula 19]
(1-17)
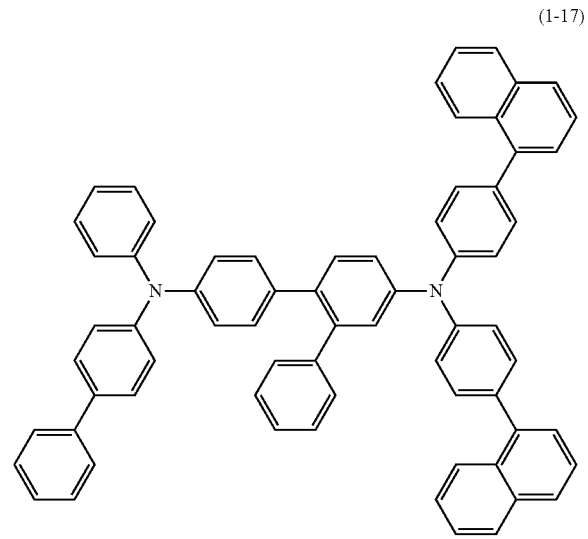
[Chemical Formula 20]
(1-18)
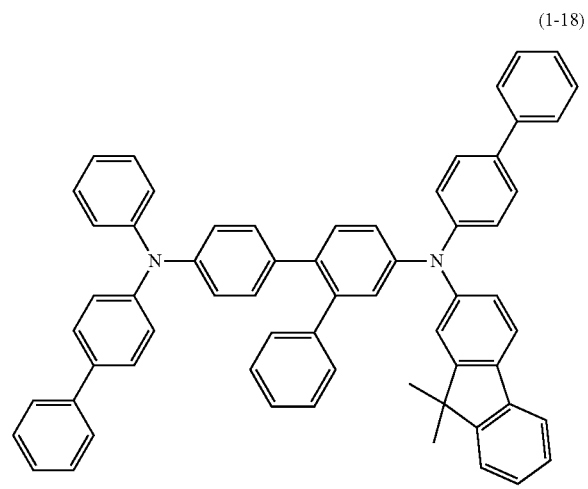
[Chemical Formula 21]
(1-19)
[Chemical Formula 22]
(1-20)
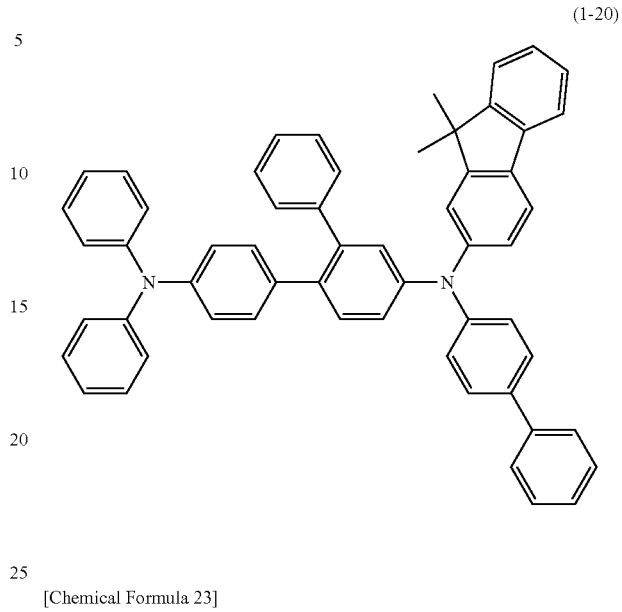
[Chemical Formula 23]
(1-21)
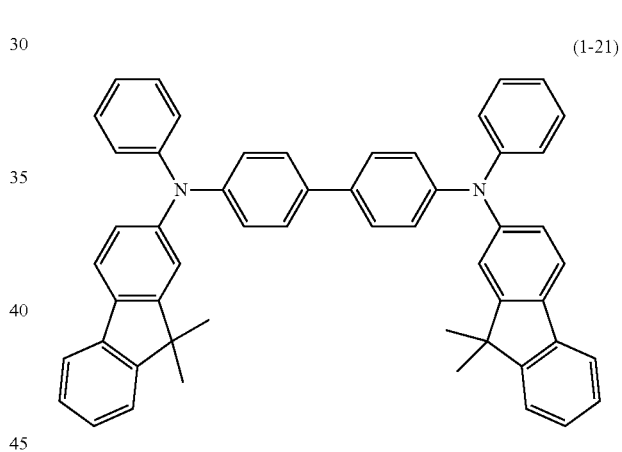
[Chemical Formula 24]
(1-22)
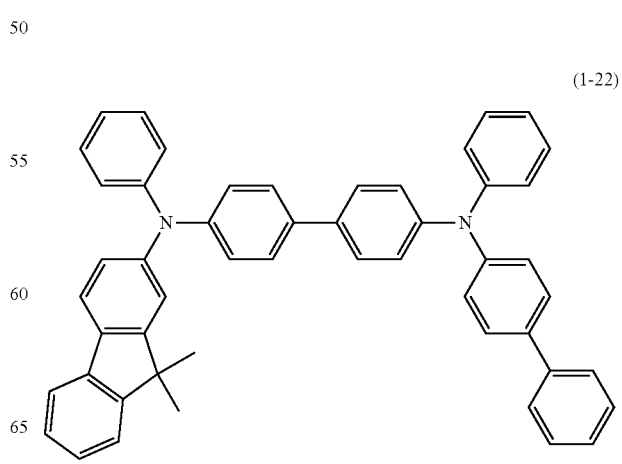

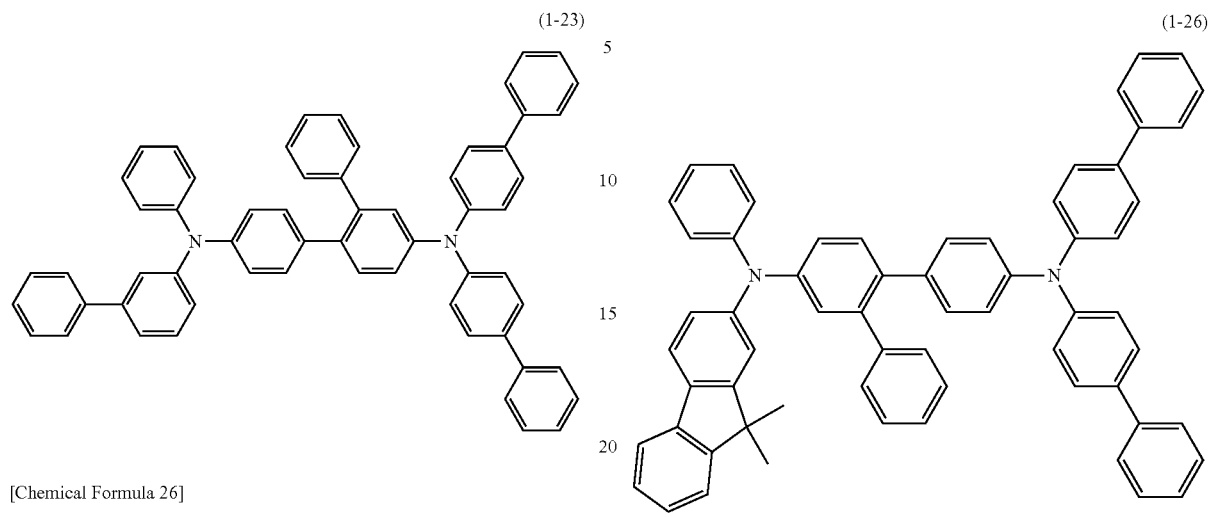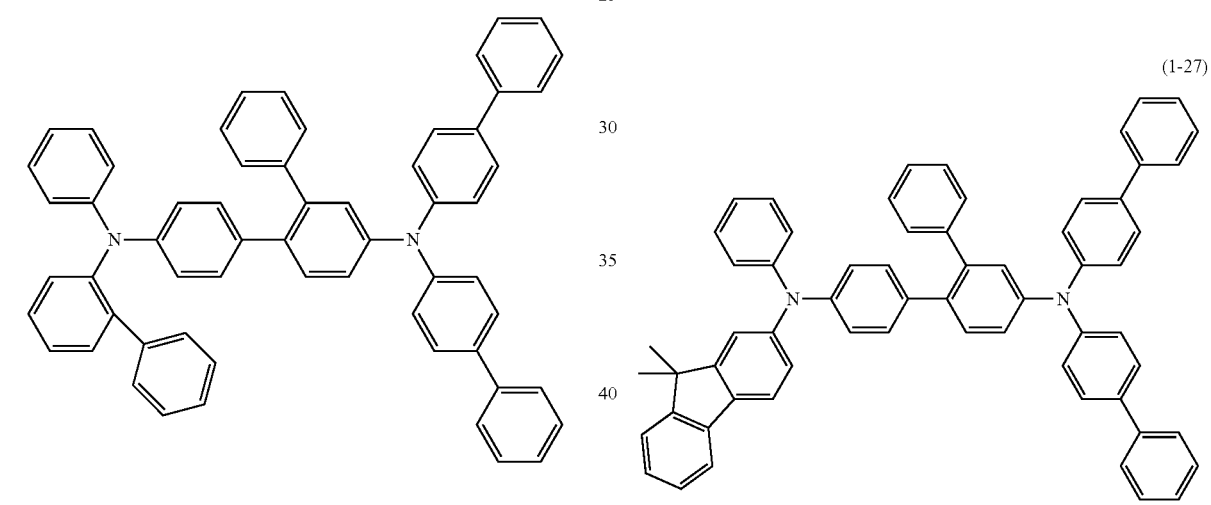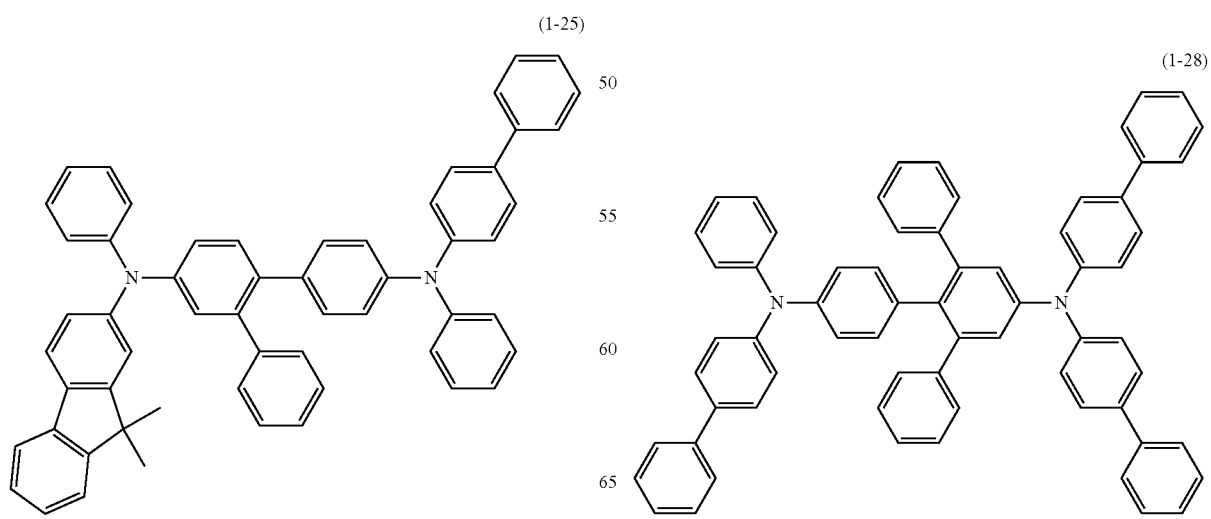

-continued

[Chemical Formula 31]

(1-29)

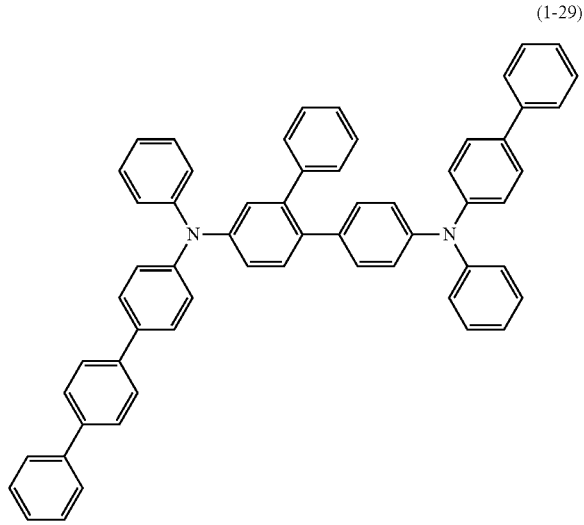

[Chemical Formula 32]

(1-30)

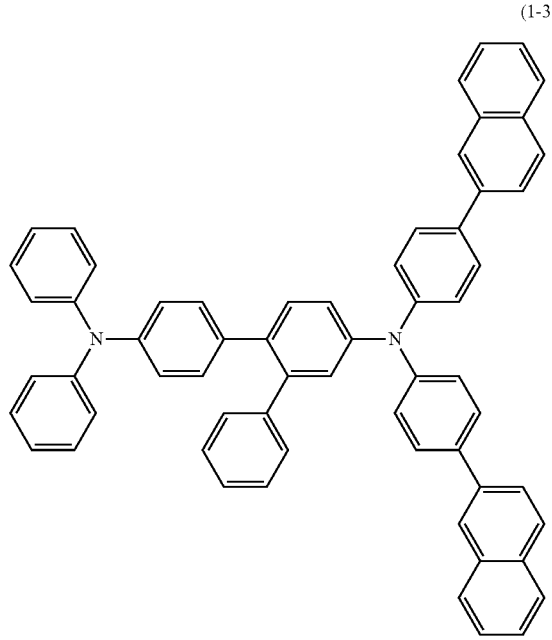

The arylamine compounds of the general formula (1) were purified by methods such as column chromatography, adsorption using, for example, a silica gel, activated carbon, or activated clay, recrystallization or crystallization using a solvent, and a sublimation purification method. The compounds were identified by an NMR analysis. A melting point, a glass transition point (Tg), and a work function were measured as material property values. The melting point can be used as an index of vapor deposition, the glass transition point (Tg) as an index of stability in a thin-film state, and the work function as an index of hole transportability and hole blocking performance.

Other compounds used for the organic EL device of the present invention were purified by methods such as column chromatography, adsorption using, for example, a silica gel, activated carbon, or activated clay, and recrystallization or crystallization using a solvent, and finally purified by a sublimation purification method.

The organic EL device of the present invention may have a structure including an anode, a hole injection layer, a hole transport layer, a light emitting layer, an electron transport layer, and a cathode successively formed on a substrate, optionally with an electron blocking layer between the hole transport layer and the light emitting layer, a hole blocking layer between the light emitting layer and the electron transport layer, and an electron injection layer between the electron transport layer and the cathode. Some of the organic layers in the multilayer structure may be omitted, or may serve more than one function. For example, a single organic layer may serve as the hole injection layer and the hole transport layer, or as the electron injection layer and the electron transport layer, and so on. Further, any of the layers may be configured to laminate two or more organic layers having the same function, and the hole transport layer may have a two-layer laminated structure, the light emitting layer may have a two-layer laminated structure, the electron transport layer may have a two-layer laminated structure, and so on. The organic EL device of the present invention is preferably configured such that the hole transport layer has a two-layer laminated structure of a first hole transport layer and a second hole transport layer.

Electrode materials with high work functions such as ITO and gold are used as the anode of the organic EL device of the present invention.

As the hole injection layer of the organic EL device of the present invention, a material obtained by p-doping an arylamine compound of the general formula (1) with a specific electron acceptor is preferably used.

As hole-injecting and transporting materials which can be mixed with or used simultaneously with the arylamine compound of the general formula (1), materials such as starburst-type triphenylamine derivatives and various triphenylamine tetramers; porphyrin compounds as represented by copper phthalocyanine; accepting heterocyclic compounds such as hexacyano azatriphenylene and coating-type polymer materials; and the like can be used. These materials may be formed into a thin film by a vapor deposition method or other known methods such as a spin coating method and an inkjet method.

Examples of material used for the hole transport layer, in addition to the arylamine compounds of the general formula (1), can be arylamine compounds having a structure in which two triphenylamine structures are joined within a molecule via a single bond or a divalent group that does not contain a heteroatom, arylamine compounds having a structure in which four triphenylamine structures are joined within a molecule via a single bond or a divalent group that does not contain a heteroatom, and various triphenylamine trimers, such benzidine derivatives as N,N'-diphenyl-N,N'-di(m-tolyl)benzidine (TPD), N,N'-diphenyl-N,N'-di(α-naphthyl)benzidine (NPD), and N,N,N',N'-tetrabiphenylylbenzidine; and 1,1-bis[4-(di-4-tolylamino)phenyl]cyclohexane (TAPC). Examples of material used for the hole injection/transport layer can be coating-type polymer materials such as poly(3,4-ethylenedioxythiophene) (PEDOT)/poly(styrene sulfonate) (PSS).

As the hole transport layer of the organic EL device of the present invention, a hole transport arylamine compound is preferably used, and the arylamine compound of the general formula (1) is preferably used. And then, the compounds that are not subjected to p-type doping are preferably used.

These may be individually deposited for film forming, and may be used as a single layer deposited mixed with other materials, or may be formed as a laminate of individually deposited layers, a laminate of mixedly deposited layers, or a laminate of an individually deposited layer and a mixedly deposited layer. These materials may be formed into a thin film by a vapor deposition method or other known methods such as a spin coating method and an inkjet method.

Examples of material used for the electron blocking layer of the organic EL device of the present invention can be compounds having an electron blocking effect, including, for example, arylamine compounds having a structure in which four triphenylamine structures are joined within a molecule via a single bond or a divalent group that does not contain a heteroatom, arylamine compounds having a structure in which two triphenylamine structures are joined within a molecule via a single bond or a divalent group that does not contain a heteroatom, carbazole derivatives such as 4,4',4"-tri(N-carbazolyl)triphenylamine (TCTA), 9,9-bis[4-(carbazol-9-yl)phenyl]fluorene, 1,3-bis(carbazol-9-yl)benzene (mCP), and 2,2-bis(4-carbazol-9-ylphenyl)adamantane (Ad-Cz); and compounds having a triphenylsilyl group and a triarylamine structure, as represented by 9-[4-(carbazol-9-yl)phenyl]-9-[4-(triphenylsilyl)phenyl]-9H-fluorene. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

In the organic EL device of the present invention, it is preferable that the electron acceptor is not subjected to p-type doping in the layer adjacent to the light emitting layer (for example, the hole transport layer and the electron blocking layer).

In the layer adjacent to the light emitting layer, an arylamine compound having a high electron blocking performance is preferably used, and the arylamine compound of the general formula (1) and the like are preferably used.

The thicknesses of these layers are not particularly limited, as far as the thicknesses are ordinarily used, and may be, for example, 20 to 100 nm for the hole transport layer, and 5 to 30 nm for the electron blocking layer.

Examples of material used for the light emitting layer of the organic EL device of the present invention can be various metal complexes such as quinolinol derivative metal complexes including $Alq_3$, anthracene derivatives, bis(styryl)benzene derivatives, oxazole derivatives, and polyparaphenylene vinylene derivatives, in addition to the amine derivative and the pyrene derivative. Further, the light emitting layer may be made of a host material and a dopant material. Examples of the host material can be thiazole derivatives, benzimidazole derivatives, and polydialkyl fluorene derivatives. Examples of the dopant material can be quinacridone, coumarin, rubrene, perylene, derivatives thereof, benzopyran derivatives, indenophenanthrene derivatives, rhodamine derivatives, and aminostyryl derivatives, in addition to the amine derivative and the pyrene derivative. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer.

Further, the light-emitting material may be a phosphorescent material. Phosphorescent materials as metal complexes of metals such as iridium and platinum may be used. Examples of the phosphorescent materials include green phosphorescent materials such as $Ir(ppy)_3$, blue phosphorescent materials such as FIrpic and FIr6, and red phosphorescent materials such as $Btp_2Ir(acac)$. Here, carbazole derivatives such as 4,4'-di(N-carbazolyl)biphenyl (CBP), TCTA, and mCP may be used as the hole injecting and transporting host material. Compounds such as p-bis(triphenylsilyl)benzene (UGH2) and 2,2',2"-(1,3,5-phenylene)-tris(1-phenyl-1H-benzimidazole) (TPBI) may be used as the electron transporting host material. In this way, a high-performance organic EL device can be produced.

In order to avoid concentration quenching, the doping of the host material with the phosphorescent light-emitting material should preferably be made by co-evaporation in a range of 1 to 30 weight percent with respect to the whole light emitting layer.

Further, examples of the light-emitting material may be delayed fluorescent-emitting material such as a CDCB derivative of PIC-TRZ, CC2TA, PXZ-TRZ, 4CzIPN or the like (refer to NPL 3, for example).

These materials may be formed into a thin-film by using a vapor deposition method or other known methods such as a spin coating method and an inkjet method.

The hole blocking layer of the organic EL device of the present invention may be formed by using hole blocking compounds such as various rare earth complexes, triazole derivatives, triazine derivatives, and oxadiazole derivatives, in addition to the metal complexes of phenanthroline derivatives such as bathocuproin (BCP), and the metal complexes of quinolinol derivatives such as aluminum(III) bis(2-methyl-8-quinolinate)-4-phenylphenolate (BAlq). These materials may also serve as the material of the electron transport layer. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Examples of material used for the electron transport layer can be metal complexes of quinolinol derivatives such as $Alq_3$ and BAlq, various metal complexes, triazole derivatives, triazine derivatives, oxadiazole derivatives, pyridine derivatives, pyrimidine derivatives, benzimidazole derivatives, thiadiazole derivatives, anthracene derivatives, carbodiimide derivatives, quinoxaline derivatives, pyridoindole derivatives, phenanthroline derivatives, and silole derivatives. These may be individually deposited for film forming, may be used as a single layer deposited mixed with other electron transporting materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Examples of material used for the electron injection layer of the organic EL device of the present invention can be alkali metal salts such as lithium fluoride and cesium fluoride; alkaline earth metal salts such as magnesium fluoride; and metal oxides such as aluminum oxide. However, the electron injection layer may be omitted in the preferred selection of the electron transport layer and the cathode.

The cathode of the organic EL device of the present invention may be made of an electrode material with a low work function such as aluminum, or an alloy of an electrode material with an even lower work function such as a magnesium-silver alloy, a magnesium-indium alloy, or an aluminum-magnesium alloy.

The following describes an embodiment of the present invention in more detail based on Examples. The present invention, however, is not restricted to the following Examples.

Example 1

Synthesis of 4,4'-bis{biphenyl-4-yl-phenylamino}biphenyl (Compound 1-1)

N-phenyl-biphenyl-4-amine (10.0 g), 4,4'-diiodobiphenyl (7.2 g), potassium carbonate (7.4 g), sodium hyposulfite (0.6 g), a copper powder (0.1 g), dodecylbenzene (7.2 mL), and xylene (7.2 mL) were added into a nitrogen-substituted reaction vessel. The mixture was stirred at 210° C. for 20 hours. Toluene was added while cooling the reaction solution, hot filtration was carried out at 50° C., and the filtrate was cooled to room temperature, then methanol was added while stirring, and the precipitated solid was collected by filtration. The obtained solid is recrystallized with toluene-methanol, whereby a yellowish white powder of 4,4'-bis{biphenyl-4-yl-phenylamino}biphenyl (Compound 1-1; 10.0 g; yield 88%) was obtained.

The structure of the obtained yellowish white powder was identified by NMR.

$^1$H-NMR (CDCl$_3$) detected 36 hydrogen signals, as follows.

δ (ppm)=7.38-7.72 (16H), 7.10-7.38 (18H), 7.07-7.08 (2H).

[Chemical Formula 33]

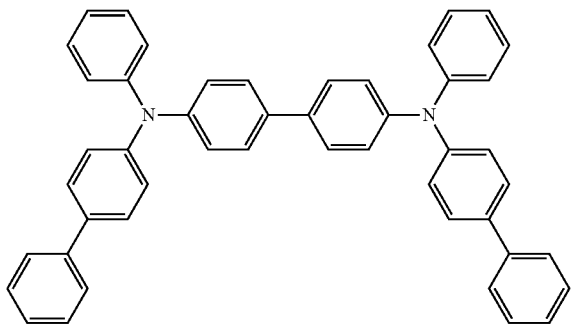

(1-1)

Example 2

Synthesis of 4-{(9,9-dimethylfluoren-2-yl)-(biphenyl-4-yl)amino}-4'-(diphenylamino)-2-phenyl-biphenyl (Compound 1-20)

(9,9-dimethylfluoren-2-yl)-(biphenyl-4-yl)-(6-bromobiphenyl-3-yl)amine (10.0 g), 4-(diphenylamino) phenylboronicacid (7.9 g), tetrakistriphenylphosphine palladium (0) (0.60 g), potassium carbonate (5.0 g), toluene (80 mL), ethanol (40 mL), and water (30 mL) were added into a nitrogen-substituted reaction vessel. The mixture was heated, and stirred at 100° C. for overnight. After cooling, an organic layer was collected by liquid separation. The organic layer was concentrated, and then purified by column chromatography (support: silica gel, eluent: dichloromethane/heptane), whereby a white powder of 4-{(9,9-dimethylfluoren-2-yl)-(biphenyl-4-yl)amino}-4'-(diphenylamino)-2-phenyl-biphenyl (Compound 1-20; 11.5 g; yield: 75%) was obtained.

The structure of the obtained white powder was identified by NMR.

$^1$H-NMR (CDCl$_3$) detected 44 hydrogen signals, as follows.

δ (ppm)=7.71-7.64 (4H), 7.58-7.56 (2H), 7.49-6.94 (32H), 1.51 (6H).

[Chemical Formula 34]

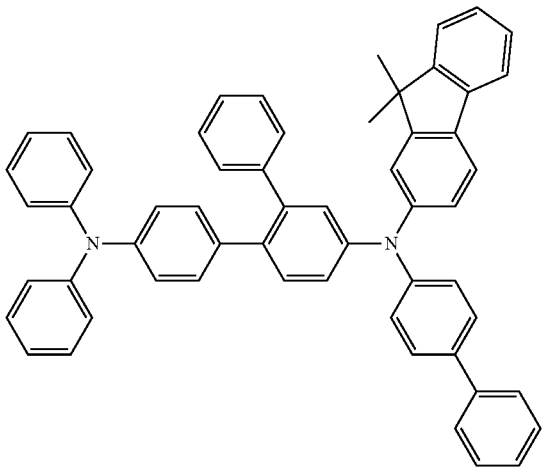

(1-20)

Example 3

Synthesis of 4,4'-bis[(9,9-dimethylfluoren-2-yl)-phenylamino]biphenyl (Compound 1-21)

4,4'-bis(phenylamino)biphenyl (10.0 g), 2-bromo-9,9-dimethylfluoren (17.1 g), toluene (100 mL), and tert-butoxy sodium (8.6 g), were added into a nitrogen-substituted reaction vessel and aerated with nitrogen gas under ultrasonic irradiation for 30 minutes. The mixture was heated after adding palladium acetate (0.1 g), a toluene solution (0.2 g) containing 50% (w/w) tert-butylphosphine, and stirred at 100° C. for 3 hours. The mixture was cooled to 80° C., hot filtration was carried out. Silica gel and activated clay were added to the filtrate to perform adsorption purification, and the solid was removed by filtration. The filtrate was concentrated and the precipitated solid was collected by filtration. The obtained solid is recrystallized with toluene, whereby a yellow powder of 4,4'-bis[(9,9-dimethylfluoren-2-yl)-phenylamino]biphenyl (Compound 1-21; 16.4 g; yield 77%) was obtained.

The structure of the obtained yellow powder was identified by NMR.

$^1$H-NMR (CDCl$_3$) detected 44 hydrogen signals, as follows.

δ (ppm)=7.62-7.65 (4H), 7.52-7.53 (4H), 7.10-7.45 (20H), 7.06-7.10 (4H), 1.47 (12H).

[Chemical Formula 35]

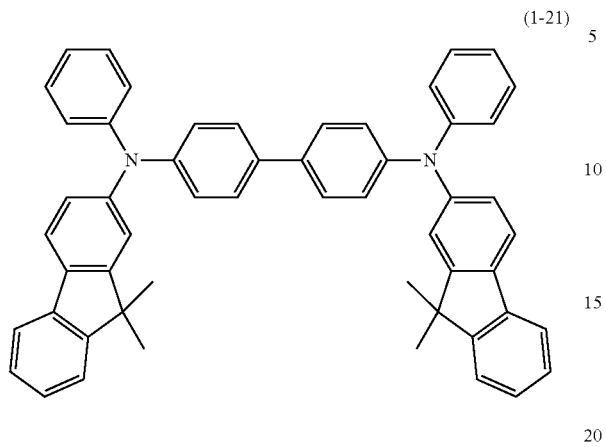

(1-21)

[Chemical Formula 36]

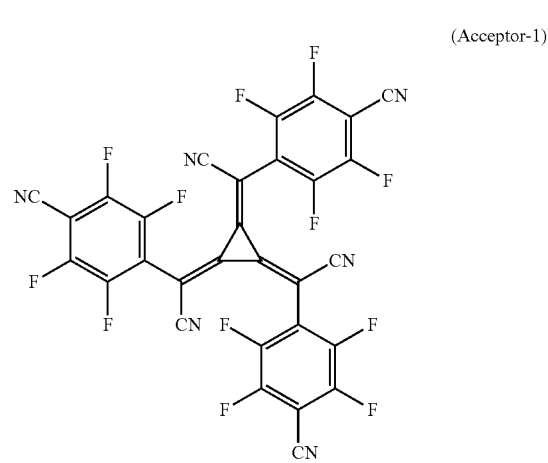

(Acceptor-1)

Example 4

The organic EL device, as shown in FIG. 1, was fabricated by vapor-depositing a hole injection layer 3, a hole transport layer 4, a light emitting layer 5, an electron transport layer 6, an electron injection layer 7, and a cathode (aluminum electrode) 8 in this order on a glass substrate 1 on which an ITO electrode was formed as a transparent anode 2 beforehand.

Specifically, the glass substrate 1 having ITO having a film thickness of 150 nm formed thereon was subjected to ultrasonic washing in isopropyl alcohol for 20 minutes and then dried for 10 minutes on a hot plate heated to 200° C. Thereafter, after performing an UV ozone treatment for 15 minutes, the glass substrate with ITO was installed in a vacuum vapor deposition apparatus, and the pressure was reduced to 0.001 Pa or lower. Subsequently, as the hole injection layer 3 covering the transparent anode 2, an electron acceptor (Acceptor-1) of the structural formula below and Compound (1-1) were formed in a film thickness of 30 nm by dual vapor deposition at a vapor deposition rate ratio of Acceptor-1/Compound (1-1)=3/97. As the hole transport layer 4 on the hole injection layer 3, Compound 1-1 was formed in a film thickness of 40 nm. As the light emitting layer 5 on the hole transport layer 4, Compound EMD-1 of the structural formula below and Compound EMH-1 of the structural formula below were formed in a film thickness of 20 nm by dual vapor deposition at a vapor deposition rate ratio of EMD-1/EMH-1=5/95. As the electron transport layer 6 on the light emitting layer 5, Compound (ETM-1) of the structural formula below and Compound (ETM-2) of the structural formula below were formed in a film thickness of 30 nm by dual vapor deposition at a vapor deposition rate ratio of Compound ETM-1/ETM-2=50/50. As the electron injection layer 7 on the electron transport layer 6, lithium fluoride was formed in a film thickness of 1 nm. Finally, aluminum was vapor-deposited in a thickness of 100 nm to form the cathode 8. The characteristics of the thus fabricated organic EL device were measured in the atmosphere at an ordinary temperature. Table 1 summarizes the results of measurement of emission characteristics when applying a DC voltage to the fabricated organic EL device.

[Chemical Formula 37]

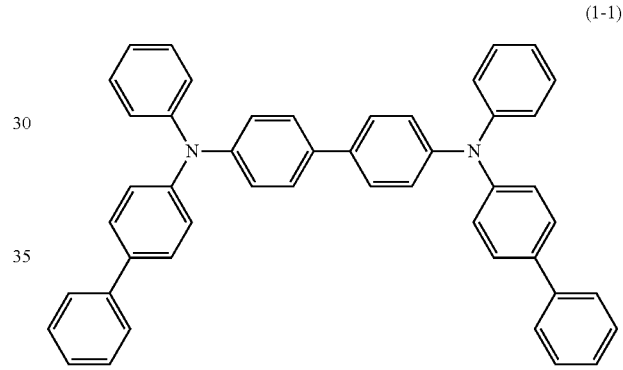

(1-1)

[Chemical Formula 38]

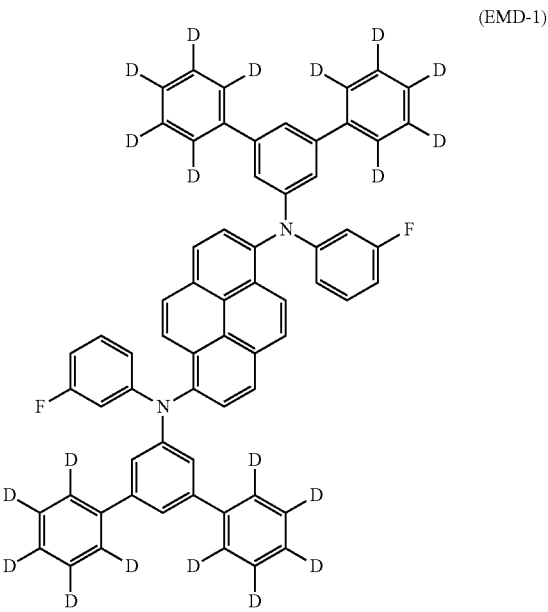

(EMD-1)

[Chemical Formula 39]

(EMH-1)

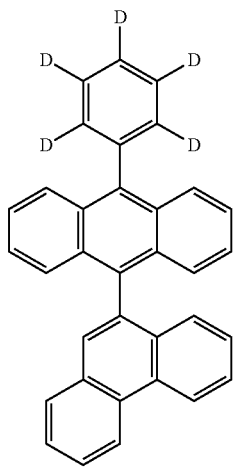

[Chemical Formula 40]

(ETM-1)

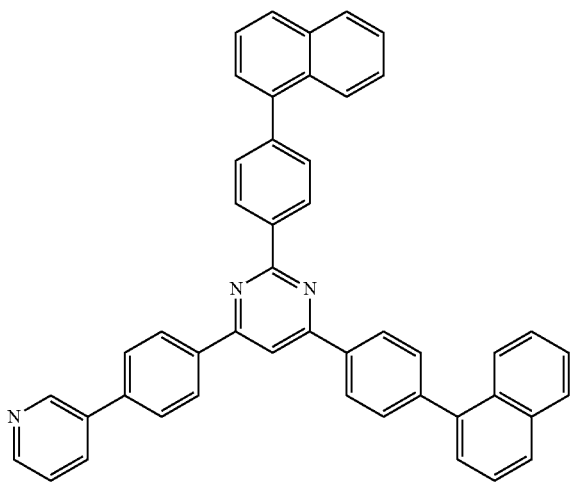

[Chemical Formula 41]

(ETM-2)

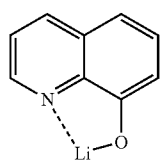

Example 5

An organic EL device was fabricated under the same conditions used in Example 4, except that the hole injection layer and the hole transport layer were formed by forming Compound (1-20), instead of using Compound (1-1). The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 42]

(1-20)

Example 6

An organic EL device was fabricated under the same conditions used in Example 4, except that the hole injection layer and the hole transport layer were formed by forming Compound (1-21), instead of using Compound (1-1). The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 43]

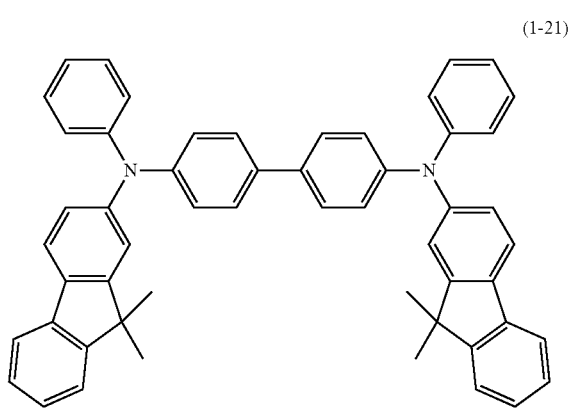

(1-21)

Comparative Example 1

For comparison, an organic EL device was fabricated under the same conditions used in Example 4, except that the hole injection layer and the hole transport layer were formed by forming Compound (HTM-1) of the structural formula below, instead of using Compound (1-1). The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 44]

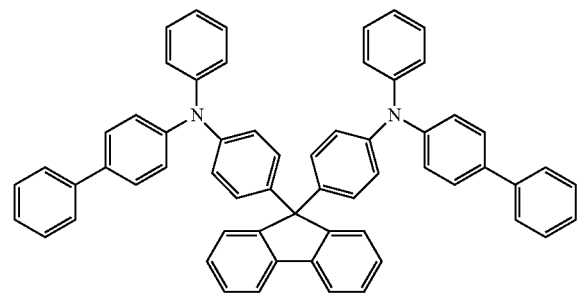

(HTM-1)

Comparative Example 2

For comparison, an organic EL device was fabricated under the same conditions used in Example 4, except that the hole injection layer and the hole transport layer were formed by forming Compound (HTM-2) of the structural formula below, instead of using Compound (1-1). The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 45]

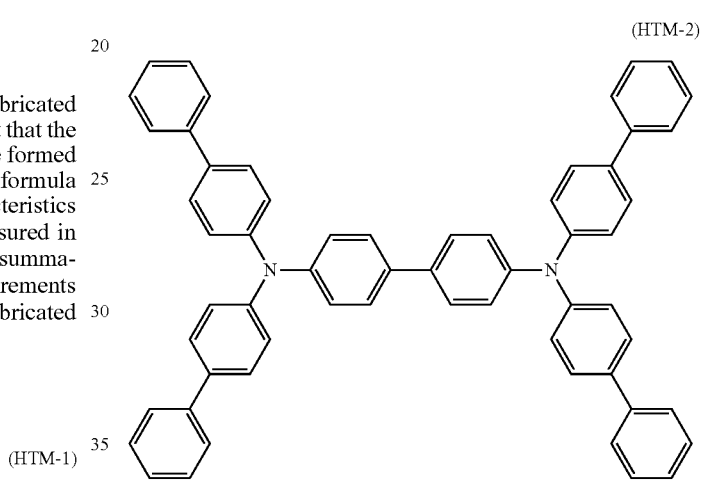

(HTM-2)

Table 1 summarizes the results of measurement of a device lifetime using the organic EL devices fabricated in Examples 4 to 6 and Comparative Examples 1 and 2. The device lifetime was measured as a time elapsed until the emission luminance of 2,000 cd/m² (initial luminance) at the start of emission was attenuated to 1,900 cd/m² (corresponding to 95% when taking the initial luminance as 100%: Attenuation to 95%) when carrying out constant current driving.

TABLE 1

|  | Hole injection layer | Hole transport layer | Voltage [V] (@10 mA/cm²) | Luminance [cd/m²] (@10 mA/cm²) | Luminous efficiency [cd/A] (@10 mA/cm²) | Power efficiency [lm/W] (@10 mA/cm²) | Lifetime of device, attenuation to 95% |
|---|---|---|---|---|---|---|---|
| Example 4 | Compound 1-1/ Acceptor-1 | Compound 1-1 | 3.60 | 831 | 8.31 | 7.24 | 361 hours |
| Example 5 | Compound 1-20/ Acceptor-1 | Compound 1-20 | 3.60 | 870 | 8.70 | 7.58 | 343 hours |
| Example 6 | Compound 1-21/ Acceptor-1 | Compound 1-21 | 3.59 | 838 | 8.38 | 7.35 | 325 hours |
| Comparative Example 1 | HTM-1/ Acceptor-1 | HTM-1 | 3.72 | 810 | 8.10 | 6.84 | 269 hours |
| Comparative Example 2 | HTM-2/ Acceptor-1 | HTM-2 | 3.67 | 804 | 8.04 | 6.89 | 277 hours |

As shown in Table 1, it was understood as follows in the comparison of Example 4 to 6, and Comparative Example 1 and 2. The luminous efficiency upon passing a current with a current density of 10 mA/cm² was 8.31 to 8.70 cd/A for the organic EL devices in Examples 4 to 6, which was higher than 8.04 to 8.10 cd/A for the organic EL devices in Comparative Examples 1 and 2. Further, the power efficiency was 7.24 to 7.58 lm/W for the organic EL devices in Examples 4 to 6, which was higher than 6.84 to 6.89 lm/W for the organic EL devices in Comparative Examples 1 and 2. Table 1 also shows that the device lifetime (attenuation to 95%) was 325 to 361 hours for the organic EL devices in Examples 4 to 6, showing achievement of a far longer lifetime than 269 to 277 hours for the organic EL devices in Comparative Examples 1 and 2.

It has been found that in the organic EL devices of the present invention, holes can be efficiently injected and transported from the anode to the hole transport layer by selecting the specific arylamine compound as the material of the hole injection layer, and subjecting to p-doping with a specific electron acceptor, and the carrier balance in the organic EL device can be improved to achieve an organic EL device having a higher luminous efficiency and a longer lifetime than the conventional organic EL devices.

INDUSTRIAL APPLICABILITY

The organic EL devices of the present invention with the combination of the specific arylamine compound and the specific electron acceptor that achieves elaborate carrier balance in the organic EL device has an improved luminous efficiency and an improved durability of the organic EL device, and can be applied, for example, to home electric appliances and illuminations.

1 Glass substrate
2 Transparent anode
3 Hole injection layer
4 Hole transport layer
5 Light emitting layer
6 Electron transport layer
7 Electron injection layer
8 Cathode

The invention claimed is:

1. An organic electroluminescent device comprising at least an anode, a hole injection layer, a hole transport layer, a light emitting layer, an electron transport layer, and a cathode, in this order, wherein the hole injection layer includes an arylamine compound represented by the following general formula (1) and a radialene derivative represented by the following general formula (2):

[Chemical Formula 1]

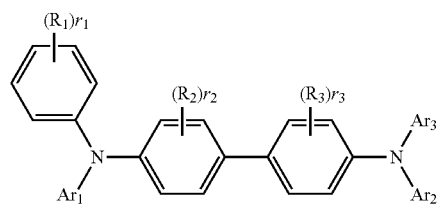

(1)

wherein $R_1$ represents a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent; $R_2$ and $R_3$ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy; $r_1$ to $r_3$ may be the same or different, $r_1$ representing 0 to 5, and $r_2$ and $r_3$ representing 0 to 4, where when $r_1$ is 2 to 5, or when $r_2$ and $r_3$ are 2 to 4, $R_1$ to $R_3$, a plurality of which bind to the same benzene ring, may be the same or different and may bind to each other via a single bond, substituted or unsubstituted methylene, an oxygen atom, or a sulfur atom to form a ring; $Ar_1$ to $Ar_3$ may be the same or different, and represent a substituted or unsubstituted phenyl, a substituted or unsubstituted biphenylyl, a substituted or unsubstituted terphenylyl, a substituted naphthyl, a substituted or unsubstituted anthracenyl, a substituted or unsubstituted phenanthrenyl, a substituted or unsubstituted fluorenyl, a substituted or unsubstituted indenyl, a substituted or unsubstituted pyrenyl, a substituted or unsubstituted perylenyl, a substituted or unsubstituted fluoranthenyl, a substituted or unsubstituted triphenylenyl, a substituted or unsubstituted pyridyl, a substituted or unsubstituted pyrimidinyl, a substituted or unsubstituted triazinyl, a substituted or unsubstituted furyl, a substituted or unsubstituted pyrrolyl, a substituted or unsubstituted thienyl, a substituted or unsubstituted quinolyl, a substituted or unsubstituted isoquinolyl, a substituted or unsubstituted benzofuranyl, a substituted or unsubstituted benzothienyl, a substituted or unsubstituted indolyl, a substituted or unsubstituted carbazolyl, a substituted or unsubstituted benzoxazolyl, a substituted or unsubstituted benzothiazolyl, a substituted or unsubstituted quinoxalinyl, a substituted or unsubstituted benzoimidazolyl, a substituted or unsubstituted pyrazolyl, a substituted or unsubstituted dibenzofuranyl, a substituted or unsubstituted dibenzothienyl, a substituted or unsubstituted naphthyridinyl, a substituted or unsubstituted phenanthrolinyl, a substituted or unsubstituted acridinyl, or a substituted or unsubstituted carbolinyl, and wherein, when $Ar_1$ to $Ar_3$ in the general formula (1) have the substituents, the substituents of $Ar_1$ to $Ar_3$ in the general formula (1) are one or more of cyano; nitro; a halogen atoms; a linear or a branched alkyloxy of 1 to 6 carbon atoms; an aryloxy; an arylalkyloxy; an aromatic hydrocarbon group, a condensed polycyclic aromatic group, or an aromatic heterocyclic group;

[Chemical Formula 2]

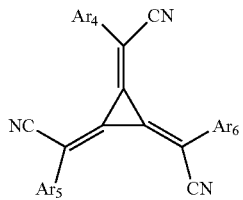

(2)

wherein Ar$_4$ to Ar$_6$ may be the same or different, and represent an aromatic hydrocarbon group, an aromatic heterocyclic group, or a condensed polycyclic aromatic group, having an electron acceptor group as a substituent;

and wherein the hole transport layer includes an arylamine compound represented by the general formula (1).

2. The organic electroluminescent device according to claim 1, wherein Ar$_1$ to Ar$_3$ in the general formula (1) represent a substituted or unsubstituted phenyl, a substituted or unsubstituted biphenylyl, or a substituted or unsubstituted terphenylyl, and wherein, when Ar$_1$ to Ar$_3$ in the general formula (1) have the substituents, the substituents of Ar$_1$ to Ar$_3$ in the general formula (1) are one or more of cyano; nitro; a halogen atoms; a linear or a branched alkyloxy of 1 to 6 carbon atoms; an aryloxy; an arylalkyloxy; an aromatic hydrocarbon group, a condensed polycyclic aromatic group, or an aromatic heterocyclic group.

3. The organic electroluminescent device according to claim 1, wherein Ar$_1$ to Ar$_3$ in the general formula (1) represent substituted or unsubstituted phenyl, substituted or unsubstituted biphenylyl, substituted or unsubstituted terphenylyl, or substituted or unsubstituted fluorenyl.

* * * * *